United States Patent
Sekiguchi

(10) Patent No.: US 10,696,957 B2
(45) Date of Patent: Jun. 30, 2020

(54) SACCHARIFICATION ENZYME COMPOSITION, SACCHARIFICATION REACTION SOLUTION, AND SUGAR PRODUCTION METHOD

(71) Applicant: NISSAN CHEMICAL INDUSTRIES, LTD., Tokyo (JP)

(72) Inventor: Kazutoshi Sekiguchi, Sodegaura (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 263 days.

(21) Appl. No.: 15/328,229

(22) PCT Filed: Jul. 28, 2015

(86) PCT No.: PCT/JP2015/071416
§ 371 (c)(1),
(2) Date: Jan. 23, 2017

(87) PCT Pub. No.: WO2016/021447
PCT Pub. Date: Feb. 11, 2016

(65) Prior Publication Data
US 2017/0218350 A1 Aug. 3, 2017

(30) Foreign Application Priority Data
Aug. 7, 2014 (JP) ................... 2014-161788

(51) Int. Cl.

| | |
|---|---|
| C12N 9/24 | (2006.01) |
| C12P 19/14 | (2006.01) |
| C13K 1/02 | (2006.01) |
| D21C 5/00 | (2006.01) |
| C12N 11/14 | (2006.01) |
| C12P 19/02 | (2006.01) |
| C12N 9/42 | (2006.01) |
| D21C 11/00 | (2006.01) |

(52) U.S. Cl.
CPC ............ *C12N 9/2437* (2013.01); *C12N 11/14* (2013.01); *C12P 19/02* (2013.01); *C12P 19/14* (2013.01); *C12Y 302/01004* (2013.01); *C13K 1/02* (2013.01); *D21C 5/005* (2013.01); *D21C 11/0007* (2013.01)

(58) Field of Classification Search
None
See application file for complete search history.

(56) References Cited

U.S. PATENT DOCUMENTS

| | | | |
|---|---|---|---|
| 4,202,939 A | 5/1980 | Mueller et al. | |
| 2014/0147885 A1 | 5/2014 | Mis et al. | |

FOREIGN PATENT DOCUMENTS

| | | |
|---|---|---|
| JP | S54-49392 A | 4/1979 |
| JP | S63-2595 A | 1/1988 |
| JP | S63-21475 B2 | 5/1988 |
| JP | H10-66594 A | 3/1998 |
| JP | 2006-136263 A | 6/2006 |
| JP | 2009-125006 A | 6/2009 |
| KR | 2014-0076140 A | 6/2014 |
| WO | 2014/195898 A1 | 12/2014 |

OTHER PUBLICATIONS

Afsahi et al., "Immobilization of Cellulase on Non-Porous Ultrane Silica Particles", Scientia Iranica, 2007, vol. 14, No. 4, pp. 379-383.*
Lupoi et al., "Evaluation of Nanoparticle-Immobilized Cellulase for Improved Ethanol Yield in Simultaneous Saccharification and Fermentation Reactions," Biotechnology and Bioengineering, vol. 108, No. 12, Dec. 2011, pp. 2835-2843.
Nov. 27, 2017 Extended Search Report issued in European Patent Application No. 15829969.3.
Baker, Carolyn S., et al., "Adsorption of Thermomonospora fusca E5 and Trichoderma reesei Cellobiohydrolase I Cellulases on Synthetic Surfaces", Applied Biochemistry and Biotechnology, vol. 94, pp. 29-40, (2001).
Oct. 27, 2015 International Search Report issued in Patent Application No. PCT/JP2015/071416.

\* cited by examiner

*Primary Examiner* — Suzanne M Noakes
(74) *Attorney, Agent, or Firm* — Oliff PLC

(57) ABSTRACT

The saccharification reaction mixture can saccharify at least one of cellulose and hemicellulose and contains, in a dispersion state, at least one of cellulose and hemicellulose, a saccharification enzyme, and colloidal silica. The ratio of the amount of the saccharification enzyme not immobilized on colloidal silica to the entire amount of the saccharification enzyme is 25% to 100%.

3 Claims, 4 Drawing Sheets

# US 10,696,957 B2

Figure 1:
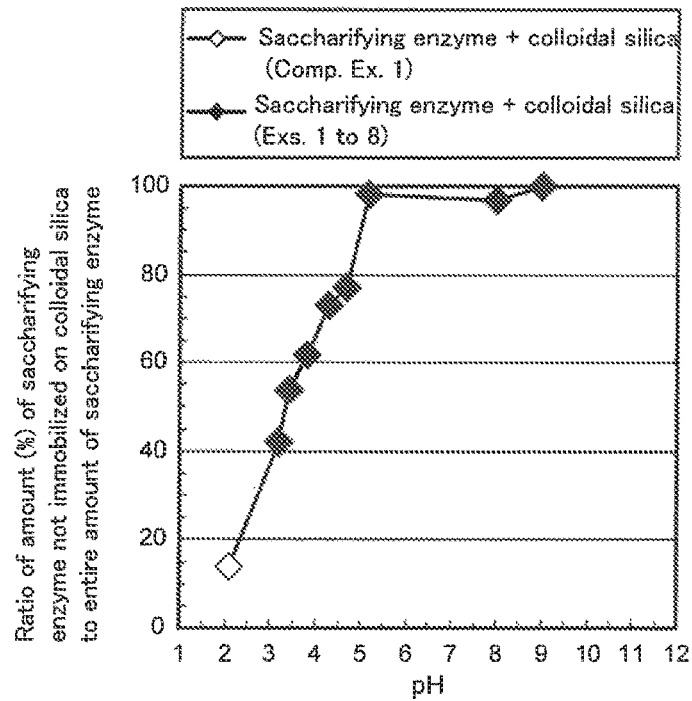

SACCHARIFICATION ENZYME COMPOSITION, SACCHARIFICATION REACTION SOLUTION, AND SUGAR PRODUCTION METHOD

TECHNICAL FIELD

The present invention relates to a saccharification enzyme composition, to a saccharification reaction mixture, and to a method for producing a saccharide (or sugar).

BACKGROUND ART

Hitherto, there has been known cellulosic bioethanol, which is produced from biomass materials containing cellulose or hemicellulose.

There has also been known a method for producing a saccharide (e.g., glucose) from cellulosic biomass materials containing cellulose or hemicellulose (i.e., a saccharification technique). In the method, the cellulosic biomass materials are hydrolyzed with sulfuric acid. The method involves problems such as corrosion of a reactor and treatment of wastewater. In another known saccharification method, cellulosic biomass materials are saccharified in the presence of a solid acid catalyst formed of a support (e.g., carbon or zeolite) on which sulfa groups are present. This method also has problems of a considerably slow reaction rate due to solid reaction and difficulty in separation of the solid acid catalyst from the unreacted residue. Furthermore, in the above methods, difficulty is encountered in controlling hydrolysis. When the hydrolysis reaction proceeds excessively, the formed saccharide decomposes, to thereby lower the yield of the saccharide of interest.

Also, enzymatic saccharification is known to be performed in the presence of an enzyme (see Patent Document 1). Such a method includes a hydrothermal step of treating a raw material with pressurized hot water, a mechanical crushing step of the hydrothermal treatment product, and a saccharifying step of saccharifying the mechanically crushed product. However, according to the method, enzymatic saccharification rate is low, whereby the produced saccharified liquid concentration is not always sufficient, which problematic.

In order to solve the problem, there has been proposed an improved method which can promote enzymatic reaction more efficiently. In the method, the enzyme is immobilized into the meso-porous of a meso-porous silica in the reaction, whereby the enzyme is caused to be present in the reaction system at a higher concentration, as compared with the case in which the enzyme is dissolved in the reaction system (see Patent Document 2). However, this method involves some problems. Specifically, the method requires an additional step of causing the enzyme to be adsorbed into the support for immobilization, and the thus-immobilized enzyme may attain a reduced reaction efficiency of only about 40 to about 50%, as compared with the case of the same enzyme in a non-immobilized state. Furthermore, difficulty is encountered in separating the enzyme-fixed support from the unreacted residue, due to the solid-solid phase reaction.

Also known is a powder form immobilized enzyme prepared by mixing an enzyme with silica sol, gelling the silica to a corresponding silica gel, and crushing the product (see Patent Documents 3 and 4). Even when such a powder-form immobilized enzyme is employed, the enzyme can be recovered, but the reaction efficiency is poor in another known method, dietary fiber containing cellulose is hydrolyzed with a mixture of an enzyme and a silica powder having a particle size of 0.5 μm to 100 μm. However, the effect of mixing the silica powder cannot be definitely proven, and difficulty is encountered in separating the suspended silica powder from the unreacted residue (see Patent Document 5).

PRIOR ART DOCUMENTS

Patent Documents

Patent Document 1: Japanese Patent Application Laid-Open (kokai) No. 2006-136263
Patent Document 2: Japanese Patent Application Laid-Open (kokai) No. 2009-125006
Patent Document 3: Japanese Patent Publication (kokoku) No 1988-2595
Patent Document 4: Japanese Patent Publication. (kokoku) No. 1988-21475
Patent Document 5: Japanese Patent Application Laid-Open (kokai) No. 1998-66594

SUMMARY OF THE INVENTION

Problems to be Solved by the Invention

Under such circumstances, the present invention has been accomplished. Thus, objects of the present invention are to provide a saccharification enzyme composition, a saccharification reaction mixture, and a method for producing a saccharide (or a sugar) (hereinafter may be referred to as a saccharide (or sugar) production method), which are aimed to enhance saccharification rate by use of an enzyme in a simple step.

Means for Solving the Problems

Accordingly, a first mode of the present invention, in order to attain the objects, is directed to a saccharification reaction mixture, characterized in that the reaction mixture which can saccharify at least one of cellulose and hemicellulose and which comprises, in a dispersion state, at least one of cellulose and hemicellulose, a saccharification enzyme, and colloidal silica, wherein the ratio of the amount of the saccharification enzyme not immobilized on colloidal silica to the entire amount of the saccharification enzyme is 25% to 100%.

Preferably, the colloidal silica has a mean primary particle size of 1 nm to 400 nm, and a particle size, as measured through a dynamic light scattering method, of 5 nm or greater and less than 500 nm.

Preferably, the reaction mixture has a saccharification enzyme concentration of 0.005 mass % to 3.0 mass %.

Preferably, the reaction mixture has a colloidal silica concentration of 0.005 mass % to 40 mass %.

Preferably, the ratio by mass of the saccharification enzyme to the colloidal silica (saccharification enzyme/colloidal silica) is 0.002 to 300.

Preferably, the reaction mixture has a pH of 3 to 11.

Preferably, the saccharification enzyme contains at least one of an enzyme derived from the genus *Aspergillus* or the genus *Trichoderma*.

A second mode of the present invention is to provide a saccharification enzyme composition, characterized in that the composition can saccharify at least one of cellulose and hemicellulose and comprises, in a dispersion state, a saccharification enzyme and colloidal silica which has a mean primary particle size of 1 nm to 400 nm, and a particle size, as measured through a dynamic light scattering method, of 5 nm or greater and less than 500 nm, wherein the ratio of the saccharification enzyme not immobilized on colloidal silica to the entire amount of the saccharification enzyme is 25% to 100%.

A third mode of the present invention is to provide a saccharide production method, characterized in that the method comprises employing the aforementioned saccharification reaction mixture, to thereby form a saccharide.

Preferably, saccharification temperature is performed at 5° C. to 100° C.

BRIEF DESCRIPTION OF THE INVENTION

FIG. 1 A graph showing the pH dependency of the ratio of the amount of the saccharification enzyme not immobilized on colloidal silica to the entire amount of the saccharification enzyme, contained in the saccharifying composition.

Figure 2:
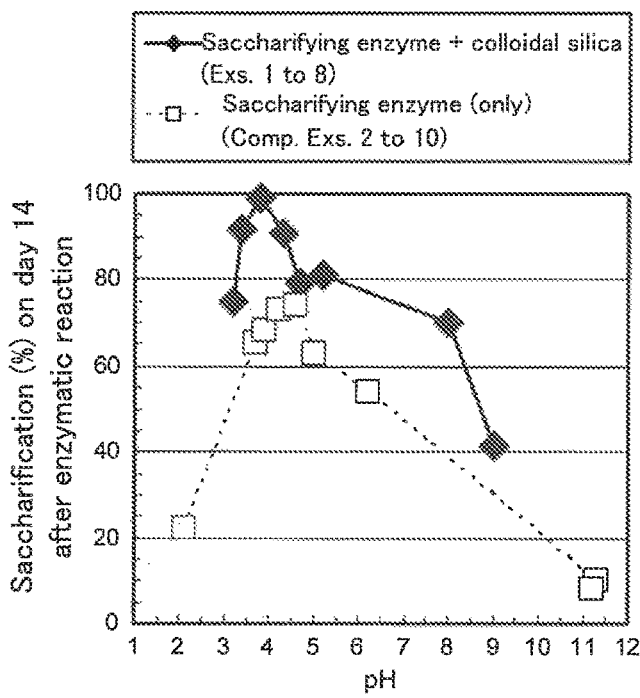

FIG. 2 A graph showing the pH dependency of the saccharification rate of the saccharification reaction mixture on day 14 after enzymatic reaction.

Figure 3:
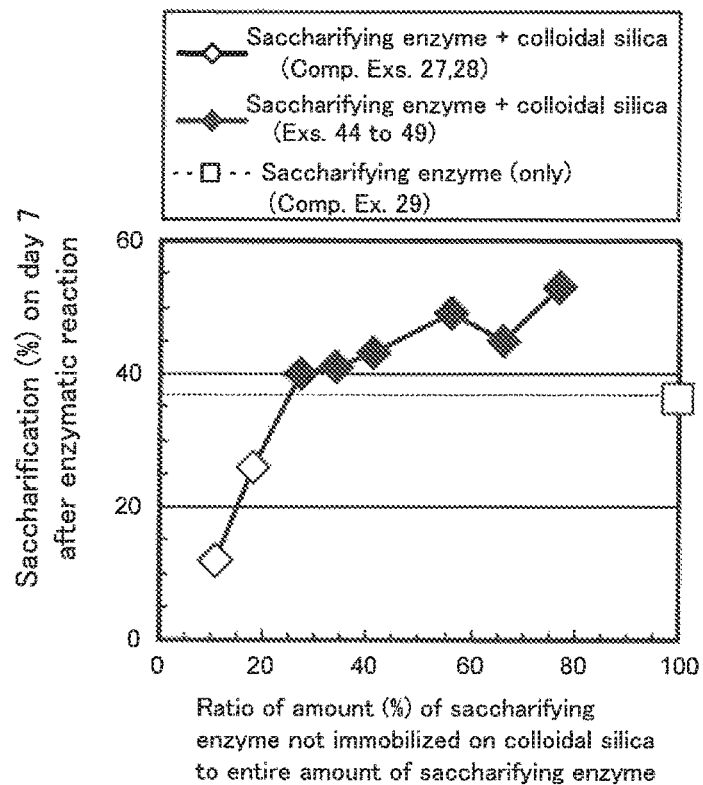

FIG. 3 A graph showing the dependency of the saccharification rate of the saccharification reaction mixture on day 7 after enzymatic reaction, on the ratio of the amount of the saccharification enzyme not immobilized on colloidal silica contained in the saccharification composition to the entire amount of the saccharification enzyme contained therein.

Figure 4:
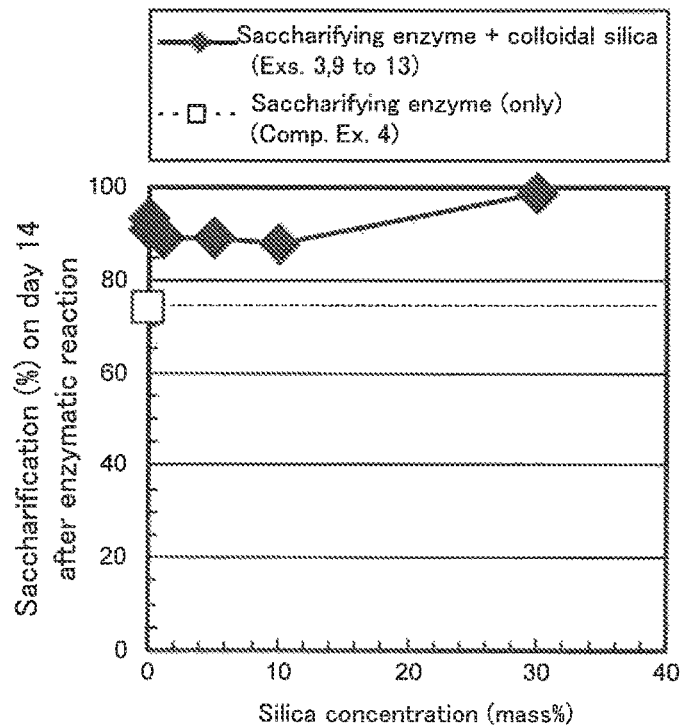

FIG. 4 A graph showing the silica concentration dependency of the saccharification rate of the saccharification reaction mixture on day 14 after enzymatic reaction.

Figure 5:
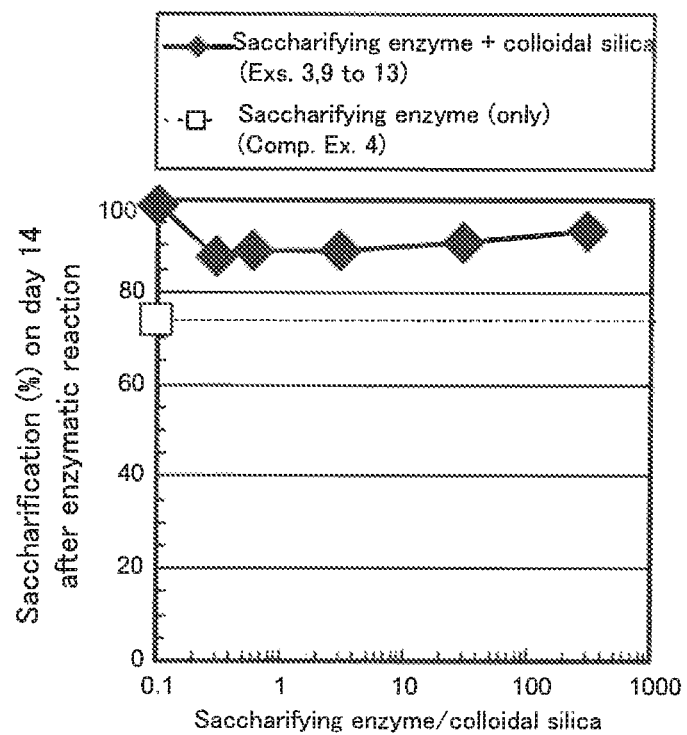

FIG. 5 A graph showing the variation of the saccharification rate of the saccharification reaction mixture on day 14 after enzymatic reaction, within a saccharification enzyme/colloidal silica ratio range of 0.1 to 300.

Figure 6:
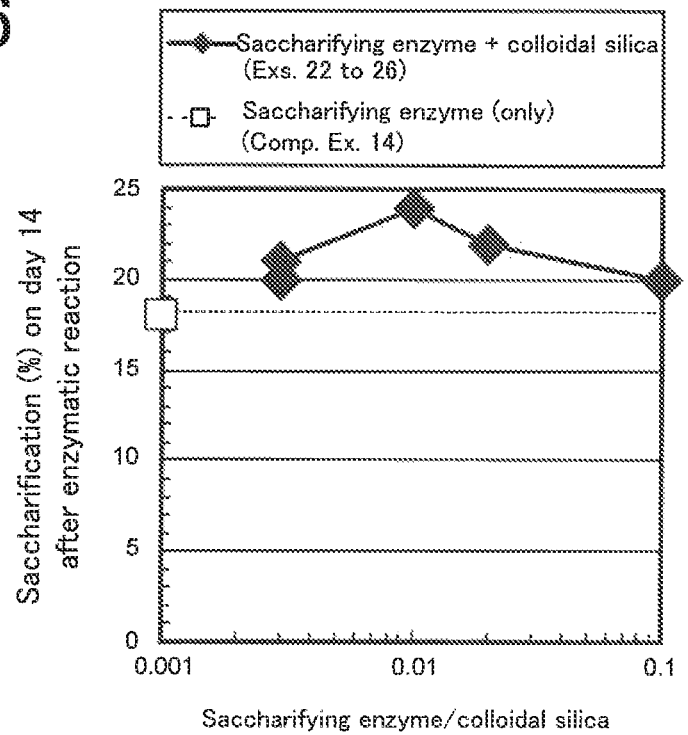

FIG. 6 A graph showing the variation of the saccharification rate of the saccharification reaction mixture on day 14 after enzymatic reaction, within a saccharification enzyme/colloidal silica ratio range of 0.003 to 0.1.

Figure 7:
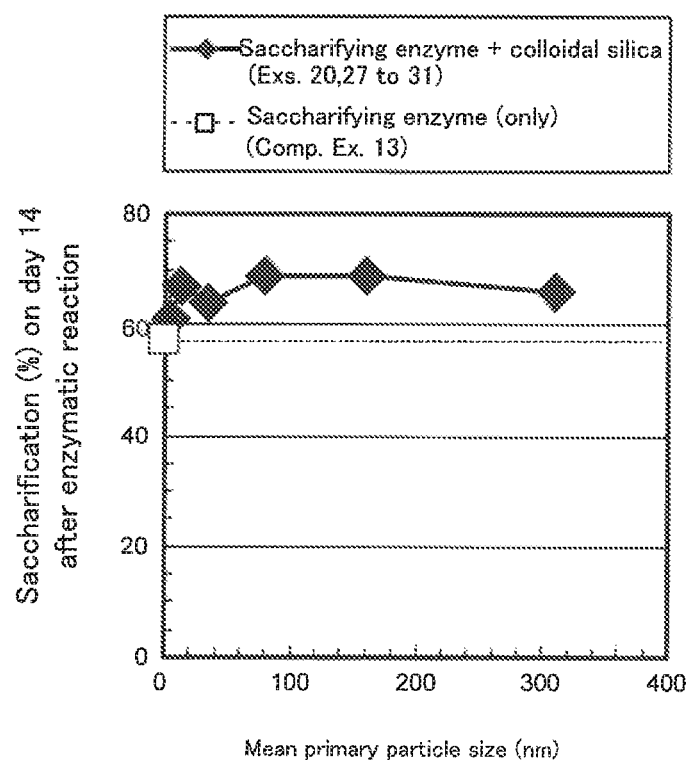

FIG. 7 A graph showing the dependency of the saccharification rate of the saccharification reaction mixture on day 14 after enzymatic reaction, on mean primary particle size.

MODES FOR CARRYING OUT THE INVENTION

In the present invention, at least one of cellulose and hemicellulose is used as a raw material.

Generally, the cellulose or hemicellulose is contained in cellulosic biomass materials such as agricultural, forest, and fishery products (e.g., broad-leaved trees and coniferous trees) and wastes thereof. Specific examples include bagasse, rice straw, corn stover, oil palm empty fruit bunches, wood fiber, wood chips, veneer waste chips, sawdust, pulp, waste paper, cotton, sea squirt, and acetic acid bacteria. No particular limitation is imposed on the biomass material, so long as it is derived from a cellulose material. Such biomass materials may be used singly or in combination of two or more species.

Among them, cellulose and hemicellulose derived from sawdust of eucalyptus wood (broad-leaved tree), sawdust of Japanese cedar (coniferous tree), bagasse, rice straw, corn stover, oil palm empty fry it bunches, and cotton are preferred. Although no precise mechanism has been elucidated, these preferred materials are easy to fibrillate, leading to high-yield sugar production.

As used herein, "cellulose" refers to a polymer formed through polymerization of glucose molecules via β-1,4-glucoside bonds, and "hemicellulose" refers to a water-insoluble polysaccharide other than cellulose, which polysaccharide is a polymer formed through polymerization of glucose molecules of glucose, xylose, mannose, galactose, etc. via glucoside bonds The cellulose may include cellooligosaccharide or cellobiose, which is a partial decomposition product of cellulose, and may be crystalline or non-crystalline. Also, the cellulose may be a carboxymethylated, aldehydified, or esterified derivative. Notably, as mentioned above, particular limitation is imposed on the species of cellulose and hemicellulose, so long as they are derived from a biomass material. Thus, the cellulose or hemi cellulose may be derived from plants, fungi, or bacteria.

In the present invention, an enzyme predominantly contains cellulase is used as the saccharification enzyme. The cellulase refers to an enzyme which decomposes cellulose or hemicellulose to a saccharide such as glucose.

No particular limitation is imposed on the microorganism which provides such a saccharification enzyme. Examples of the microorganism include bacteria belonging to the genus *Acremonium*, to the genus *Aspergillus*, to the genus *Chaetomium*, to the genus *Fusarium*, to the genus *Humicola*, to the genus *Irpex*, to the genus *Phanerochaete*, to the genus *Penicillium*, to the genus *Schizophyllum*, to the genus *Sporotrichum*, to the genus *Trametes*, and to the genus *Trichoderma*. Examples of the microorganism also include bacteria belonging to the genus *Clostridium*, to the genus *Pseudomonas*, to the genus *Cellulomonas*, to the genus *Ruminococcus*, and to the genus *Bacillus*, and actinomycetes belonging to the genus *Sulfolobus*, to the genus *Streptomyces*, to the genus *Thermoactinomyces*, and to the genus *Thermomonospora*. These enzymes may be artificially modified and may be used singly or in combination of two or more species.

Among them, enzymes derived from bacteria belonging to the genus *Aspergillus* and to the genus *Trichoderma* are preferred, since they have high enzymatic activity on crystalline cellulose.

Alternatively, the cellulose may be a group of enzymes. The enzyme group includes endoglucanase (EC 3.2.1.74), cellobiohydrase (EC 3.2.1.91), β-glucosidase (EC 23.2.4.1, EC 3.2.1.21), etc. Notably, cellulases derived from different bacterial species are preferably used in combination. In this case, saccharification of cellulose or hemicellulose can be more promoted by virtue of the synergistic effect.

The aforementioned cellulase generally has an optimum enzymatic activity at a pH of 3 to 6. However, the cellulose may be an alkaline cellulase, having an optimum enzymatic activity at a pH of 6 to 10. Also, the aforementioned cellulase generally has an optimum enzymatic activity at a reaction temperature of 25° C. to 50° C. However, the cellulase may be a heat-resistant cellulase, having an optimum enzymatic activity at a reaction temperature of 70° C. to 100° C.

In the present invention, the colloidal silica has a mean primary particle size of 1 nm to 400 nm, preferably 5 nm to 350 nm, and is dispersed in the saccharification reaction mixture. The mean primary particle size is calculated by the formula: D (nm)=2720/S, wherein S represents a specific surface area ($m^2/g$) as determined through the nitrogen adsorption method (BET method). The entirety or a part of the colloidal silica serves as a support for the saccharification enzyme and is used in a dispersion state with a portion of the saccharification enzyme not immobilized on colloidal silica. The particle size of the colloidal silica dispersed in liquid may be represented by the particle size measured through a dynamic light scattering method. In the present invention, the particle size measured through a dynamic light scattering method is 5 nm or greater and smaller than 500 nm, preferably 10 nm to 450 nm. The silica is not porous particle, but is solid particle. In use, the colloidal silica is dispersed in a dispersion solvent such as water, methanol, ethanol, acetone, methyl ethyl ketone, or ethylene glycol, to form a dispersion liquid. The dispersion liquid is generally called colloidal liquid or sol. So long as the enzymatic activity is not inhibited, any dispersion solvent may be used. Preferably, the dispersion solvent is water or ethanol.

In contrast, silica powder which is called precipitated silica is a porous silica powder having a mean primary particle size of 400 nm or smaller, and a particle size measured through a dynamic light scattering method of 500 nm or greater. Thus, when the powder is suspended in a dispersion solvent, no colloidal property is observed. In addition, precipitated silica does not have such a high dispersibility as that of colloidal silica of the present invention.

The colloidal silica may be produced through a water glass method employing water glass as a raw material, an alkoxide method employing a metal alkoxide as a raw material, or a vapor phase method employing a silicon chloride compound as a raw material. Any of these methods may be employed to form colloidal silica, but the water glass method is preferably employed.

The saccharification reaction mixture of the present invention assumes a dispersion which contains at least one of cellulose and hemicellulose as a raw material, with a saccharification enzyme and colloidal silica, wherein the ratio of the amount of the saccharification enzyme not immobilized on colloidal silica to the entire amount of the saccharification enzyme is 25% to 100%. Preferably, the ratio of the amount of the saccharification enzyme not immobilized on colloidal silica to the entire amount of the saccharification enzyme is 50% to 100%. When the ratio of the amount of the saccharification enzyme ncot immobilized on colloidal silica to the entire amount of the saccharification enzyme is smaller than 25%, reaction efficiency is disadvantageously poor.

In the saccharification reaction mixture, the saccharification enzyme concentration is 0.005 mass % to 3.0 mass %, preferably 0.01 mass % to 1.0 mass %. When the saccharification enzyme concentration is lower than 0.005 mass %, reaction efficiency is disadvantageously poor, whereas when the saccharification enzyme concentration is higher than 3.0 mass %, dissolution of the saccharification enzyme is impeded, and cost disadvantageously increases.

In the saccharification reaction mixture, the colloidal silica concentration is 0.005 mass % to 40 mass %, preferably 0.01 mass % to 10 mass %. When the colloidal silica concentration is lower than 0.005 mass %, reaction efficiency is disadvantageously poor, whereas when the colloidal silica concentration is higher than 40 mass %, dispersibility is poor, and cost disadvantageously increases.

In the saccharification reaction mixture, the ratio by mass of the saccharification enzyme to the colloidal silica (saccharification enzyme/colloidal silica) is 0.002 to 300, preferably 0.1 to 10. When the (saccharification enzyme/colloidal silica) mass ratio falls outside the range, considerable enhancement in reaction efficiency fails to be attained.

The pH of the saccharification reaction mixture is 3 to 11, preferably 3 to 9, more preferably 4 to 7. When the pH is lower than 3, the reaction efficiency of the saccharification enzyme decreases, due to aggregation of colloidal silica, whereas when the pH is higher than 11, undesired dissolution of colloidal silica tends to occurs. Both cases are not preferred.

Examples of the pH-adjusting agents for the saccharification reaction mixture include mineral acids such as sulfuric acid, hydrochloric acid, and nitric acid; carboxylic acids such as acetic acid and oxalic acid; hydroxy acids such as citric acid, tartaric acid, and malic acid; hydroxide salts such as sodium hydroxide and potassium hydroxide; ammonia; and urea. No particular limitation is imposed on the type and concentration of the pH-adjusting agent, so long as the effects of the present invention are not impaired. Also, these pH-adjusting agents may be used singly or in combination of two or more species. Furthermore, the pH-adjusting agent may be used in a buffer having a buffering action.

The reaction temperature of the saccharification reaction mixture of the present invention is preferably 5° C. to 100° C., more preferably 20° C. to 55° C. When the reaction temperature is lower than 5° C., saccharification efficiency considerably decreases, whereas when the reaction temperature is higher than 100° C., the saccharification enzyme may be deactivated. Both cases are not preferred.

Notably, the cellulosic biomass material containing cellulose or hemicellulose may be preliminarily treated in a known manner. Generally, the biomass material may be subjected to physical crushing by means of a cutter mill or the like, an acid or alkaline treatment for chemically destructing the structures of lignin, cellulose, and hemicellulose, to thereby provide a raw material to be saccharided.

In preparation of the saccharification reaction mixture, colloidal silica may be added to the reaction mixture in which the saccharification enzyme is dispersed. Alternatively, a saccharification enzyme may be added to the reaction mixture in which colloidal silica is dispersed. So long as the effects of the present invention are not impaired, the pH-adjusting agent or the like may be added in any order.

In saccharification reaction, the saccharification enzyme and colloidal silica may be isolated from a saccharide (e.g., glucose) by means of a reverse osmotic (RO) membrane or a ultrafiltration (UF) membrane having an appropriate fraction molecular weight. The fraction molecular weight is preferably 1,000 to 100,000. When the fraction molecular weight is smaller than the lower limit of the range, a sugar of interest can be separated. However, clogging tends to occur in the separation step, thereby considerably lowering the membrane-passing rate. When the fraction molecular weight is in excess of the higher limit of the range, the saccharification enzyme and colloidal silica may be eluted along with sugar. Both cases are not preferred.

EXAMPLES

The present invention will next be described in more detail by way of examples, which should not be construed as limiting the invention thereto.

The mean primary particle size of colloidal silica and the particle size thereof measured through a dynamic light scattering method were determined by means of the following measurement apparatuses:

Apparatus in nitrogen adsorption method (determination of mean primary particle size): Monosorb MS-16 (product of Quantachrome Instruments Japan), and Particle size analyzer in dynamic light scattering method: Zetasizer Nano S (product of Malvern Instruments).

Saccharification Enzyme Compositions of Examples 1 to 7 and Comparative Example 1

Cellulase aqueous solutions (i.e., aqueous saccharification enzyme solutions) were prepared in the following manner. As a cellulase, a cellulase (product of MP biomedicals), having an optimum enzymatic activity at a pH of 3 to 6 and being derived from the *Aspergillus niger*) was used.

Firstly, cellulase powder (15 g) was added to deionized water (85 g), and the mixture was stirred at room temperature for 2 hours by means of a magnetic stirrer, to thereby prepare a 15 mass % cellulase aqueous solution. Separately, an alkaline silica sol (pH: 9.0, silica concentration: 40 mass %) (200 g), in which both solid and spherical colloidal silica. (mean primary particle size: 35 nm, and particle size measured through a dynamic light scattering method: 55 nm) prepared through the water glass method was dispersed in water, and was treated with a strongly acidic H-type cation exchange resin Amberlite (registered trademark) IR-120B (product of Organo Corporation), to thereby remove alkali metal ions. As a result, 200 g of an acidic silica sol (pH: 2.1, silica concentration: 40 mass %) was yielded. To the thus-yielded acidic silica sol (15 g), the aforementioned cellulase aqueous solution (4.0 g) was added under stirring. Further, as a pH-adjusting agent, one member (1.0 g) selected from among 1 M acetic acid, sodium acetate (hereinafter referred to as Na acetate), acetic acid-Na acetate buffer (pH: 3.5 to 5.0), 0.5M NaOH, and HCl was added thereto, to thereby prepare a saccharification enzyme composition having a silica concentration of 30 mass % and a cellulase concentration of 3 mass %. The thus-prepared saccharification enzyme composition was found to have a particle size measured through a dynamic light scattering method of 55 nm, indicating that the particle size of the colloidal silica dispersion was not changed.

Saccharification Enzyme Composition of Example 8

Both solid and spherical colloidal silica (mean primary particle size: 35 nm, particle size measured through a dynamic light scattering method: 55 nm) produced through the water glass method were dispersed in water, to thereby prepare an alkaline silica sod. (pH: 9.0, silica concentration: 40 mass %). Under stirring, the aforementioned cellulase aqueous solution (4.0 g) was added to the alkaline silica sol (15 g) For the purpose of pH adjustment, 1M Na acetate (0.5 g) and 1M NaOH (0.5 g) were added to the silica composition having a silica concentration of 30 mass % and a cellulase concentration of 3 mass %. The particle size measured through a dynamic light scattering method of the thus-yielded saccharification enzyme composition was found to be 55 nm, indicating that the particle size of the colloidal silica dispersion was not changed. Table 1 shows the saccharification enzyme compositions of Examples 1 to 8.

Determination of the Ratio of the Amount of the Saccharification Enzyme not Immobilized on Colloidal Silica to the Entire Amount of the Saccharification Enzyme In the saccharification enzyme composition of the present invention, the ratio of the amount of the saccharification enzyme not immobilized on colloidal silica to the entire amount of the saccharification enzyme was determined by centrifugating the enzyme composition and quantifying the saccharification enzyme concentration of the supernatant through the Bradford method (CBB method).

The specific procedure was as follows.

An aliquot (1.0 mL) of the saccharification enzyme composition was sampled in a 50-mL centrifuge tube, and centrifugation was performed by means of a high speed refrigerated centrifuge SRX-201 (product of Tomy Seiko Co., Ltd.) at 25,000 G at 4° C. for 30 minutes, to thereby recover a supernatant. Separately, a protein assay CBB solution (5-fold concentrated) (product of Nacalai Tesque) was 5-fold diluted with deionized water. To a disposable cell (cell length: 10 mm), the diluted CBB solution (2.5 mL) aid the supernatant (0.05 mL) were sequentially added. The disposable cell was tightly closed with the disposable cell cap, and the contents were uniformly mixed in an up and down manner repeatedly. Thereafter, the mixture was allowed to stand for 30 minutes, and the absorbance of the sample was measured at 595 nm wavelength by means of a spectrophotometer UV-3150 (product of Shimadzu Corporation). A calibration curve was drawn from absorbance measurements obtained in the same manner from concentration-known saccharification enzyme samples. The saccharification enzyme concentration of the supernatant was calculated by the thus-drawn calibration curve.

The saccharification enzyme concentration of the supernatant obtained through the above procedure was divided by the initial saccharification enzyme concentration and then multiplied by 100, to thereby provide the ratio of the amount of the saccharification enzyme not immobilized on colloidal silica to the entire amount of the saccharification enzyme. FIG. 1 shows the relationship between pH and the ratios (the amount of the saccharification enzyme not immobilized on colloidal silica to the entire amount of the saccharification enzyme) of the saccharification enzyme compositions of Examples 1 to 8. As is clear from FIG. 1, the ratio of the amount of the saccharification enzyme not immobilized on colloidal silica to the entire amount of the saccharification enzyme was found to depend upon the pH of the saccharification enzyme composition.

Saccharification Enzyme Compositions of Comparative Examples 2 to 10

The procedure of each of Examples 1 to 8 was repeated, except that the saccharification enzyme concentration was adjusted by deionized water instead of addition of colloidal silica, to thereby prepare saccharification enzyme compositions each containing no colloidal silica. Table 1 shows the saccharification enzyme compositions.

Saccharification Enzyme Composition of Comparative Example 11

An alkaline silica sol (pH: 9.0, silica concentration: 40 mass %) (20 g), in which both solid and spherical colloidal silica (mean primary particle size: 35 nm, and particle size measured through a dynamic light scattering method: 55 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 2.1, silica concentration: 40 mass %) was yielded. Deionized water (5 g) was added to the thus-yielded acidic silica sol (15 g), to thereby prepare a saccharification enzyme composition having a silica concentration of 30 mass Table 1 shows this saccharification enzyme composition.

Saccharification Reaction Mixtures of Examples 1 to 8

In each of the saccharification enzyme compositions of Examples 1 to 8, microcrystalline cellulose powder (2.5 mass %) was dispersed, to thereby prepare a saccharification reaction mixture.

The specific procedure was as follows.

Each saccharification enzyme composition (10 mL) was added to a glass bottle (20 mL) and was stirred by means of stirrer (4 mmφ, 10 mm length). To the composition under stirring, microcrystalline cellulose powder (product of MP Biomedicals) (0.25 g (equivalent to 25 mg/mL) was added. Then, the glass bottle was tightly closed.

Saccharide Production Methods of Examples 1 to 8

Each of the saccharification reaction mixtures of Examples 1 to 8 was stirred in a thermostat chamber maintained at 24° C. for 14 days (enzymatic reaction).

Enzymatic reaction temperature of each saccharification reaction mixture and saccharification rate (day 3 and day 14) as determined through the procedure described below are shown in Table 2. FIG. 2 shows the relationship between pH and the day 14 saccharification rate of each of the saccharification reaction mixtures of Examples 1 to 8.

Comparative Examples 1 to 11

Production of each saccharification reaction mixture and sugar production method were performed in the same manner as employed in Examples 1 to 8. Table 2 shows the results. Also, FIG. 2 shows the relationship between pH and the day 14 saccharification rate of each of the saccharification reaction mixtures of Comparative Examples 1 to 8. As is clear from FIGS. 1 and 2, a higher saccharification rate was attained, in all pH regions, in the case of a saccharification reaction mixture containing colloidal silica and having a ratio of the amount of the saccharification enzyme not immobilized on colloidal silica to the entire amount of the saccharification enzyme of 42% to 100%, as compared with the case of use of only a saccharification enzyme.

Determination of Saccharification Rate

Glucose concentration of each saccharification reaction mixture during enzymatic reaction was determined through an enzymatic method (G6PDH-HK method), to thereby calculate saccharification rate.

Specifically, a saccharification reaction mixture sample (0.5 mL) was collected in a 2-mL microtube and heated at 110° C. for 30 minutes, to thereby deactivate the enzyme. Subsequently, in order to remove unreacted cellulose and colloidal silica, the sample was transferred to a 50-mL centrifuge tube, and centrifugation was performed by means of a high speed refrigerated centrifuge SRX-201 (product of Tomy Seiko Co., Ltd.) at 25,000 G at 4° C. for 30 minutes. Immediately after completion of centrifugation, a supernatant was recovered. In the enzymatic method, an F-kit glucose (product of J. K. International) was used. The absorbance of the sample was measured at 340 nm wavelength (cell length: 10 mm) by means of a spectrophotometer UV-3150 (product of Shimadzu Corporation).

The specific procedure was as follows.

Specifically, an F-kit solution I (1.0 mL) was added to a disposable cell (cell length; 10 mm), and then the aforementioned supernatant (0.1 mL) and deionized water (1.9 mL) were added to the cell, followed by tightly closing the cell with the disposable cell cap. The contents of the cell were uniformly mixed in an up and down manner repeatedly. Thereafter, the mixture was allowed to stand for 3 minutes, and the absorbance ($E_1$) of the formed supernatant was measured at 340 nm wavelength by means of a spectrophotometer. Next, an F-kit solution II (0.02 mL) was added to the supernatant, and the contents of the cell were uniformly mixed in an up and down manner repeatedly. Then, the sample was allowed to stand for 15 minutes, and the absorbance ($E_2$) of the formed supernatant was measured at 340 nm wavelength by means of a spectrophotometer. The absorbance of the blank was obtained by measuring the absorbance of deionized water instead of the supernatant.

D-Glucose concentration was obtained by the following equation.

$$D\text{-Glucose [mg/mL]} = (V \times Mw \times \Delta E) / (\varepsilon \times d \times v \times 1000) \quad [F1]$$
$$= (3.02 \times 180.16 \times \Delta E)/(6.3 \times 1 \times 1 \times 1000)$$
$$= 0.864 \times \Delta E$$

$\Delta E = (E_2 - E_1)$ sample $- (E_2 - E_1)$ blank $V$ (volume of reaction mixture): 3.02 [mL]

$Mw$ (molecular weight): 180.16 [g/mol]

$d$ (optical path): 1 [cm]

$\varepsilon$ (light absorption coefficient): 6.3 [mmol$^{-1}$·cm$^{-1}$]

$v$ (volume of sample): 0.1 [mL]

Formed glucose concentration of each saccharification reaction mixture during enzymatic reaction determined through the aforementioned method was divided by the added microcrystalline cellulose powder concentration (equivalent to 25 mg/mL) and then multiplied by 100, to thereby provide the saccharification rate of the saccharification reaction mixture.

TABLE 1

| | SEn C. | | MPPS | PS | SC | SE/CS | pH-adjuster | | | Ratio |
|---|---|---|---|---|---|---|---|---|---|---|
| | SEn | mass % | nm | nm | mass % | by mass | type | concn. | pH | % |
| Comp. 1 | As. n. | 3 | 35 | 55 | 30 | 0.1 | H | 0.025M | 2.1 | 14 |
| Ex. 1 | As. n. | 3 | 35 | 55 | 30 | 0.1 | A | 0.05M | 3.2 | 42 |
| Ex. 2 | As. n. | 3 | 35 | 55 | 30 | 0.1 | B | 0.05M | 3.4 | 46 |
| Ex. 3 | As. n. | 3 | 35 | 55 | 30 | 0.1 | C | 0.05M | 3.8 | 62 |
| Ex. 4 | As. n. | 3 | 35 | 55 | 30 | 0.1 | D | 0.05M | 4.3 | 73 |
| Ex. 5 | As. n. | 3 | 35 | 55 | 30 | 0.1 | E | 0.05M | 4.7 | 77 |
| Ex. 6 | As. n. | 3 | 35 | 55 | 30 | 0.1 | F | 0.05M | 5.2 | 98 |
| Ex. 7 | As. n. | 3 | 35 | 55 | 30 | 0.1 | G | 0.025M | 8.0 | 97 |
| Ex. 8 | As. n. | 3 | 35 | 55 | 30 | 0.1 | F | 0.025M | 9.0 | 100 |
| | | | | | | | G | 0.025M | | |
| Comp. 2 | As. n. | 3 | — | — | — | — | H | 0.025M | 2.1 | 100 |
| Comp. 3 | As. n. | 3 | — | — | — | — | A | 0.05M | 3.7 | 100 |
| Comp. 4 | As. n. | 3 | — | — | — | — | B | 0.05M | 3.9 | 100 |

TABLE 1-continued

|  | SEn | SEn C. mass % | MPPS nm | PS nm | SC mass % | SE/CS by mass | pH-adjuster type | pH-adjuster concn. | pH | Ratio % |
|---|---|---|---|---|---|---|---|---|---|---|
| Comp. 5 | As. n. | 3 | — | — | — | — | C | 0.05M | 4.2 | 100 |
| Comp. 6 | As. n. | 3 | — | — | — | — | D | 0.05M | 4.6 | 100 |
| Comp. 7 | As. n. | 3 | — | — | — | — | E | 0.05M | 5.0 | 100 |
| Comp. 8 | As. n. | 3 | — | — | — | — | F | 0.05M | 6.2 | 100 |
| Comp. 9 | As. n. | 3 | — | — | — | — | G | 0.025M | 11.3 | 100 |
| Comp. 10 | As. n. | 3 | — | — | — | — | F | 0.025M | 11.2 | 100 |
|  |  |  |  |  |  |  | G | 0.025M |  | 100 |
| Comp. 11 | — | — | 35 | 55 | 30 | — | — | — | 2.1 | — |

SEn: Saccharification enzyme derived from
As. n.: *Aspergillus niger*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharification enzyme not immobilized on colloidal silica
pH-Adjuster
A: Acetic acid
B: Na acetate buffer (pH = 3.5)
C: Na acetate buffer (pH = 4.0)
D: Na acetate buffer (pH = 4.5)
E: Na acetate buffer (pH = 5.0)
F: Na acetate
G: NaOH
H: HCl

TABLE 2

|  | Reaction temp. ° C. | Saccharification rate day 3 % | Saccharification rate day 14 % |
|---|---|---|---|
| Comp. Ex. 1 | 24 | 11 | 13 |
| Ex. 1 | 24 | 38 | 75 |
| Ex. 2 | 24 | 51 | 92 |
| Ex. 3 | 24 | 54 | 99 |
| Ex. 4 | 24 | 51 | 91 |
| Ex. 5 | 24 | 40 | 79 |
| Ex. 6 | 24 | 48 | 81 |
| Ex. 7 | 24 | 32 | 70 |
| Ex. 8 | 24 | 5 | 42 |
| Comp. Ex. 2 | 24 | 14 | 22 |
| Comp. Ex. 3 | 24 | 31 | 65 |
| Comp. Ex. 4 | 24 | 39 | 68 |
| Comp. Ex. 5 | 24 | 36 | 73 |
| Comp. Ex. 6 | 24 | 33 | 74 |
| Comp. Ex. 7 | 24 | 32 | 63 |
| Comp. Ex. 8 | 24 | 25 | 54 |
| Comp. Ex. 9 | 24 | 3 | 10 |
| Comp. Ex. 10 | 24 | 5 | 8 |
| Comp. Ex. 11 | 24 | 0 | 0 |

Saccharification Enzyme Compositions of Examples 9 to 26

Through the procedure described below, a cellulase aqueous solution was prepared as a saccharification enzyme aqueous solution. As the cellulase, a cellulase which has an optimum enzymatic activity at a pH of 3 to 6 and which is derived from the *Aspergillus niger* (product of MP biomedicals) was used.

Firstly, a cellulase powder (10 g) was added to deionized water (90 g), and the powder was dissolved at room temperature for 2 hours by means of a magnetic stirrer, to thereby prepare a 10 mass % cellulase aqueous solution. Separately, an alkaline silica sol (pH: 9.0, silica concentration: 40 mass %) (200 q), in which both solid and spherical colloidal silica (mean primary particle size: 35 nm, and particle size measured through a dynamic light scattering method: 55 nm) prepared through the water glass method was dispersed in water, was treated with a strongly acidic H-type cation exchange resin Amberlite (registered trademark) IR-120B (product of Organo Corporation), to thereby remove alkali metal ions. As a result, 200 g of an acidic silica sol (pH: 2.1, silica concentration: 40 mass %) was yielded. To the thus-yielded acidic silica sol, deionized water and the aforementioned 10 mass % cellulase aqueous solution were added under stirring. Further, as a pH-adjusting agent, 1M acetic acid-Na acetate buffer (pH: 4.0) (0.05 M) was added thereto, to thereby prepare a saccharification enzyme composition having a silica concentration of 0.01 to 38 mass % and a cellulase concentration of 0.1 to 3 mass %. The thus-prepared saccharification enzyme composition was found to have a particle size measured through a dynamic light scattering method of 55 nm, indicating that the particle size of the colloidal silica dispersion was not changed.

Table 3 shows the saccharification enzyme compositions of Examples 9 to 26

Saccharification Enzyme Compositions of Comparative Examples 12 to 14

The procedure of each of Examples 9 to 26 was repeated, except that the saccharification enzyme concentration was adjusted by deionized water instead of addition of colloidal silica, to thereby prepare saccharification enzyme compositions each containing no colloidal silica. Table 3 shows the saccharification enzyme compositions.

Production of each saccharification reaction mixture, the sugar production method, and determination of saccharification reaction efficiency were performed in the same manner as employed in Examples 1 to 8. Table 4 shows the results of saccharification rate measurement. Also, FIG. 4 shows the relationship between silica concentration and the day 14 saccharification rate of each of the saccharification reaction mixtures of Examples 3, and 9 to 13, and Comparative Example 4. As is clear from FIG. 4, a high saccharification rate was attained when the silica concentration was 0.01 to 30 mass %, in the case of a saccharification reaction mixture having a ratio of the amount of the saccharification enzyme not immobilized on colloidal silica to the entire amount of the saccharification enzyme is 25% to 100%. Thus, a higher saccharification rate was attained, as compared with the case where the saccharification reaction mixture contained no colloidal silica. In Example 22, even when the silica concentration was 38 mass %, a high saccharification rate was attained. Thus, a higher saccharification rate was attained, as compared with the case where the saccharification reaction mixture contained no colloidal silica.

Furthermore, a high saccharification rate was attained when the saccharification enzyme concentration was 0.1 to 3.0 mass %, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

Also, FIG. 5 shows the relationship between the saccharification enzyme to colloidal silica mass ratio (saccharification enzyme/colloidal silica) and the day 14 saccharification rate of each of the saccharification reaction mixtures of Examples 3, and 9 to 13, and Comparative Example 4.

FIG. 6 shows the relationship between the saccharification enzyme to colloidal silica mass ratio (saccharification enzyme/colloidal silica) and the day 14 saccharification rate of each of the saccharification reaction mixtures of Examples 22 to 26, and Comparative Example 14.

As is clear from FIGS. 5 and 6, a high saccharification rate was attained when the saccharification enzyme to colloidal silica mass ratio (saccharification enzyme/colloidal silica) was 0.003 to 300, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

FIG. 7 shows the relationship between the primary particle size and the day 14 saccharification rate of each of the saccharification reaction mixtures of Examples 20 and 27 to 31, and Comparative Example 13. As is clear from FIG. 7, a high saccharification rate was attained when the mean primary particle size of colloidal silica was 5 nm to 310 nm, in the case of a saccharification reaction mixture having a ratio of the amount of the saccharification enzyme not immobilized on colloidal silica to the entire amount of the saccharification enzyme of 25 to 100%. Thus, a higher saccharification rate was attained, as compared with the case where the saccharification reaction mixture contained no colloidal silica.

TABLE 3

| | SEn | SEn C. mass % | MPPS nm | PS nm | SC mass % | SE/CS by mass | pH-adjuster type | pH-adjuster concn. | pH | Ratio % |
|---|---|---|---|---|---|---|---|---|---|---|
| Ex. 3 | As. n. | 3 | 35 | 55 | 30 | 0.1 | C | 0.05M | 3.8 | 62 |
| Ex. 9 | As. n. | 3 | 35 | 55 | 10 | 0.3 | C | 0.05M | 4.1 | 82 |
| Ex. 10 | As. n. | 3 | 35 | 55 | 5 | 0.6 | C | 0.05M | 4.1 | 79 |
| Ex. 11 | As. n | 3 | 35 | 55 | 1 | 3 | C | 0.05M | 4.2 | 95 |
| Ex. 12 | As. n. | 3 | 35 | 55 | 0.1 | 30 | C | 0.05M | 4.2 | 99 |
| Ex. 13 | As. n | 3 | 35 | 55 | 0.01 | 300 | C | 0.05M | 4.2 | 100 |
| Comp. 5 | As. n | 3 | — | — | — | — | C | 0.05M | 4.2 | 100 |
| Ex. 14 | As. n. | 1 | 35 | 55 | 30 | 0.03 | C | 0.05M | 3.8 | 80 |
| Ex. 15 | As. n. | 1 | 35 | 55 | 10 | 0.1 | C | 0.05M | 4.0 | 80 |
| Ex. 16 | As. n. | 1 | 35 | 55 | 5 | 0.2 | C | 0.05M | 4.1 | 77 |
| Ex. 17 | As. n. | 1 | 35 | 55 | 1 | 1 | C | 0.05M | 4.1 | 83 |
| Comp. 12 | As. n. | 1 | — | — | — | — | C | 0.05M | 4.1 | 100 |
| Ex. 18 | As. n. | 0.5 | 35 | 55 | 30 | 0.02 | C | 0.05M | 3.8 | 79 |
| Ex. 19 | As. n. | 0.5 | 35 | 55 | 10 | 0.05 | C | 0.05M | 4.0 | 78 |
| Ex. 20 | As. n. | 0.5 | 35 | 55 | 5 | 0.1 | C | 0.05M | 4.1 | 86 |
| Ex. 21 | As.n. | 0.5 | 35 | 55 | 1 | 0.5 | C | 0.05M | 4.1 | 78 |
| Comp. 13 | As. n. | 0.5 | — | — | — | — | C | 0.05M | 4.1 | 100 |
| Ex. 22 | As. n. | 0.1 | 35 | 55 | 38 | 0.003 | C | 0.05M | 3.5 | 98 |
| Ex. 23 | As. n. | 0.1 | 35 | 55 | 30 | 0.003 | C | 0.05M | 3.7 | 95 |
| Ex. 24 | As. n. | 0.1 | 35 | 55 | 10 | 0.01 | C | 0.05M | 4.0 | 93 |
| Ex. 25 | As. n. | 0.1 | 35 | 55 | 5 | 0.02 | C | 0.05M | 4.0 | 88 |
| Ex. 26 | As. n | 0.1 | 35 | 55 | 1 | 0.1 | C | 0.05M | 4.1 | 73 |
| Comp. 14 | As. n. | 0.1 | — | — | — | — | C | 0.05M | 4.1 | 100 |

SEn: Saccharification enzyme derived from
As. n.: *Aspergillus niger*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharifaction enzyme not immobilized on colloidal silica
pH-Adjuster
C: Na acetate buffer (pH = 4.0)

TABLE 4

| | Reaction temp. °C. | Saccharification rate day 3 % | Saccharification rate day 14 % |
|---|---|---|---|
| Ex. 3 | 24 | 54 | 99 |
| Ex. 9 | 24 | 49 | 88 |
| Ex. 10 | 24 | 51 | 89 |
| Ex. 11 | 24 | 53 | 89 |
| Ex. 12 | 24 | 58 | 91 |
| Ex. 13 | 24 | 68 | 93 |
| Comp. Ex. 5 | 24 | 36 | 73 |
| Ex. 14 | 24 | 48 | 85 |
| Ex. 15 | 24 | 48 | 79 |
| Ex. 16 | 24 | 43 | 80 |
| Ex. 17 | 24 | 37 | 77 |
| Comp. Ex. 12 | 24 | 30 | 72 |
| Ex. 18 | 24 | 40 | 72 |
| Ex. 19 | 24 | 37 | 72 |
| Ex. 20 | 24 | 32 | 65 |
| Ex. 21 | 24 | 35 | 65 |
| Comp. Ex. 13 | 24 | 19 | 57 |
| Ex. 22 | 24 | 10 | 20 |
| Ex. 23 | 24 | 13 | 21 |
| Ex. 24 | 24 | 12 | 24 |
| Ex. 25 | 24 | 11 | 22 |
| Ex. 26 | 24 | 10 | 20 |
| Comp. Ex. 14 | 24 | 8 | 18 |

Saccharification Enzyme Composition of Example 27

A cellulase aqueous solution (i.e., a saccharification enzyme aqueous solution) was prepared in the following manner. As a cellulase, a cellulase (product of MP biomedicals), having an optimum enzymatic activity at a pH of 3 to 6 and being derived from the *Aspergillus niger*) was used.

Specifically, both solid and spherical colloidal silica (mean primary particle size: 5 nm, particle size measured through a dynamic light scattering method: 15 nm) produced through the water glass method were dispersed in water, to thereby prepare an acidic silica sol (pH: 2.8, silica concentration: 10 mass %). Under stirring, deionized water (8.0 g) and the aforementioned 10 mass % cellulase aqueous solution (1.0 g) were added to the acidic silica sol (10 g). For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %. The particle size measured through a dynamic light scattering method of the thus-yielded saccharification enzyme composition was found to be 15 nm, indicating that the particle size of the colloidal silica dispersion was not changed.

Saccharification Enzyme Composition of Example 28

Both solid and spherical colloidal silica (mean primary particle size: 12 nm, particle size measured through a dynamic light scattering method: 20 nm) produced through the water glass method were dispersed in water, to thereby prepare an acidic silica sol (pH: 2.6, silica concentration: 20 mass %). Under stirring, deionized water (13.0 g) and the aforementioned 10 mass % cellulase aqueous solution (1.0 g) were added to the acidic silica sol (5.0 g). For the purpose of pH adjustment, 1M acetic acid-Na acetate buffer (pH: 4) (1.0 g) was added to the silica sol mixture, to thereby yield a saccharification enzyme composition having a silica concentration of 5 mass % and a cellulase concentration of 0.5 mass %. The particle size measured through a dynamic light scattering method of the thus-yielded saccharification enzyme composition was found to be 20 nm, indicating that the particle size of the colloidal silica dispersion was not changed.

Saccharification Enzyme Composition of Example 29

An alkaline silica sol (pH: 9.5, silica concentration: 40 mass %) (20 g), in which both solid and spherical colloidal silica (mean primary particle size: 80 nm, and particle size measured through a dynamic light scattering method: 120 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 2.0, silica concentration: 40 mass %) was yielded. To the thus-yielded acidic silica sol (2.5 g), deionized water (15.5 g) and the aforementioned 10 mass % cellulase aqueous solution (1.0 g) were added under stirring. For the purpose of pH adjustment, 1M acetic acid-Na acetate buffer (pH: 4) (1.0 g) was added to the silica sol mixture, to thereby yield a saccharification enzyme composition having a silica concentration of 5 mass % and a cellulase concentration of 0.5 mass %. The particle size measured through a dynamic light scattering method of the thus-yielded saccharification enzyme composition was found to be 120 nm, indicating that the particle size of the colloidal silica dispersion was not changed.

Saccharification Enzyme Composition of Example 30

An alkaline silica sol (pH: 9.3, silica concentration: 40 mass %) (20 g), in which both solid and spherical colloidal silica (mean primary particle size: 160 nm, and particle size measured through a dynamic light scattering method: 200 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 2.3, silica ($SiO_2$) concentration: 40 mass %) was yielded. To the thus-yielded acidic silica sol (2.5 g), deionized water (15.5 g) and the aforementioned 10 mass % cellulase aqueous solution (1.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %. The particle size measured through a dynamic light scattering method of the thus-yielded saccharification enzyme composition was found to be 200 nm, indicating that the particle size of the colloidal silica dispersion was not changed.

Saccharification Enzyme Composition of Example 31

An alkaline silica sol (pH: 8.5, silica concentration: 40 mass %) (20 g), in which both solid and spherical colloidal silica (mean primary particle size: 310 nm, and particle size measured through a dynamic light scattering method: 450 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 3.3, silica concentration: 40 mass %) was yielded. To the thus-yielded acidic silica sol (2.5 g), deionized water (15.5 g) and the aforementioned 10 mass % cellulase aqueous solution (1.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %. The particle size measured through a dynamic light scattering method of the thus-yielded saccharification enzyme composition was found to be 450 nm, indicating that the particle size of the colloidal silica dispersion was not changed.

Table 5 shows the saccharification enzyme compositions of Examples 27 to 31.

Production of each saccharification reaction mixture, sugar production method, and determination of saccharification reaction efficiency were performed in the same manner as employed in Examples 1 to 8. Table 6 shows the results of saccharification rate measurement.

optimum enzymatic activity at a pH of 3 to 6 and being derived from the *Trichoderma reesei*) was used.

Firstly, cellulase powder (1 g) was added to deionized water (9 g), and the mixture was stirred at room temperature for 2 hours by means of a magnetic stirrer, to thereby prepare a 10 mass cellulase aqueous solution. Separately, an alkaline silica sol (pH: 9.0, silica concentration: 40 mass %) (20 g), in which both solid and spherical colloidal silica (mean primary particle size: 35 nm, and particle size measured through a dynamic light scattering method: 55 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 2.1, silica concentration: 40 mass %) was yielded. To the thus-yielded acidic silica sol, deionized water and the aforementioned 10 mass % cellulase aqueous solution were added under stirring. For the purpose of pH adjustment, 1M acetic acid-Na acetate buffer (pH: 4.0) (0.05 M) was added to the silica sol mixture, to thereby yield a saccharification enzyme composition having a silica concentration of 0.01 to 10 mass % and a cellulase concentration of 0.01 to 1 mass %. The particle size measured through a dynamic light scattering method of

TABLE 5

| | SEn | SEn C. mass % | MPPS nm | PS nm | SC mass % | SE/CS by mass | pH-adjuster type | | pH | Ratio % |
|---|---|---|---|---|---|---|---|---|---|---|
| Ex. 27 | As. n. | 0.5 | 5 | 15 | 5 | 0.1 | C | 0.05M | 4.1 | 98 |
| Ex. 28 | As. n. | 0.5 | 12 | 20 | 5 | 0.1 | C | 0.05M | 4.1 | 91 |
| Ex. 20 | As. n. | 0.5 | 35 | 55 | 5 | 0.1 | C | 0.05M | 4.1 | 86 |
| Ex. 29 | As. n. | 0.5 | 80 | 120 | 5 | 0.1 | C | 0.05M | 4.1 | 88 |
| Ex. 30 | As. n. | 0.5 | 160 | 200 | 5 | 0.1 | C | 0.05M | 4.1 | 92 |
| Ex. 31 | As. n. | 0.5 | 310 | 450 | 5 | 0.1 | C | 0.05M | 4.1 | 80 |
| Comp. 13 | As. n. | 0.5 | — | — | — | — | C | 0.05M | 4.1 | 100 |

SEn: Saccharification enzyme derived from
As. n.: *Aspergillus niger*
SEn C.: Saccharification enzyme concentration
MPPS: Mean primary particle size
PS: Particle size measured through dynamic light scatteringmethod
SC: Silica concentration
SE/CS: Saccharification enzyme/colloidal silica
Ratio: the ratio of the amount of the saccharification enzyme not immobilized on colloidal silica
pH-Adjuster
C: Na acetate buffer (pH = 4.0)

TABLE 6

| | Reaction temp. ° C. | Saccharification rate day 3 % | Saccharification rate day 14 % |
|---|---|---|---|
| Ex. 27 | 24 | 28 | 61 |
| Ex. 28 | 24 | 34 | 67 |
| Ex. 20 | 24 | 32 | 65 |
| Ex. 29 | 24 | 33 | 69 |
| Ex. 30 | 24 | 34 | 69 |
| Ex. 31 | 24 | 15 | 66 |
| Comp. Ex. 13 | 24 | 19 | 57 |

Saccharification Enzyme Compositions of Examples 32 to 37

Cellulase aqueous solutions (i.e., saccharification enzyme aqueous solutions) prepared in the following manner. As a cellulase, a cellulase (product of Sigma Aldrich), having an the thus-yielded saccharification enzyme composition was found to be 55 nm, indicating that the particle size of the colloidal silica dispersion was not changed.

Table 7 shows the saccharification enzyme compositions of Examples 32 to 37

Saccharification Enzyme Compositions of Comparative Examples 15 to 20

The procedure of each of Examples 32 to 37 was repeated, except that the saccharification enzyme concentration was adjusted by deionized water instead of addition of colloidal silica. Table 7 shows the saccharification enzyme compositions.

Production of each saccharification reaction mixture, sugar production method, and determination of saccharification reaction efficiency were performed in the same manner as employed in Examples 1 to 8. Table 8 shows the results of saccharification rate measurement.

A high saccharification rate was attained by use of a cellulase derived from the *Trichoderma reesei* as well as a cellulase derived from the *Aspergillus niger*, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

A high saccharification rate was attained when the silica concentration was 0.01 to 10 mass %, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

Furthermore, a high saccharification rate was attained when the saccharification enzyme concentration was 0.01 to 1.0 mass %, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

Saccharification Enzyme Compositions of Examples 38 to 43

Cellulase aqueous solutions (i.e., saccharification enzyme aqueous solutions) were prepared in the following manner. As a cellulase, a cellulase (product of Sigma Aldrich), having an optimum enzymatic activity at a pH of 3 to 6 and being derived from the *Trichoderma reesei*) was used.

Firstly, cellulase powder (0.5 g) was added to deionized water (9.5 g), and the mixture was stirred at room temperature for 2 hours by means of a magnetic stirrer, to thereby prepare a 5 mass % cellulase aqueous solution. Separately, an alkaline silica sol (pH: 9.0, silica concentration: 40 mass %) (20 g), in which both solid and spherical colloidal silica (mean primary particle size: 35 nm, and particle size measured through a dynamic light scattering method: 55 nm) prepared through the water glass method was dispersed in water, was treated with a strongly acidic H-type cation exchange resin Amberlite (registered trademark) IR-120B (product of Organo Corporation), to thereby remove alkali metal ions. As a result, 20 g of an acidic silica sol (pH: 2.1, silica concentration: 40 mass %) was yielded. To the thus-yielded acidic silica sol, deionized water and the aforementioned 5 mass % cellulase aqueous solution were added under stirring. For the purpose of pH adjustment, a 1M acetic acid-Na acetate buffer (pH: 4.0 to 6.0) (0.05 M) was added to the silica sol mixture, to thereby yield a saccharification enzyme composition having a silica concentration of 5 mass % and a cellulase concentration of 0.01 to 0.5 mass %. The particle size measured through a dynamic light scattering method of the thus-yielded saccharification enzyme composition was found to be 55 nm, indicating that the particle size of the colloidal silica dispersion was not changed.

Table 9 shows the saccharification enzyme compositions of Examples 38 to 43.

Saccharification Enzyme Compositions of Comparative Examples 21 to 26

The procedure of each of Examples 38 to 43 was repeated, except that the saccharification enzyme concentration was

TABLE 7

| | SEn | SEn C. mass % | MPPS nm | PS nm | SC mass % | SE/CS by mass | pH-adjuster type | concn | pH | Ratio % |
|---|---|---|---|---|---|---|---|---|---|---|
| Ex. 32 | Td. r. | 1 | 35 | 55 | 10 | 0.1 | C | 0.05M | 4.0 | 26 |
| Ex. 33 | Td. r. | 0.5 | 35 | 55 | 5 | 0.1 | C | 0.05M | 4.1 | 49 |
| Ex. 34 | Td. r. | 0.1 | 35 | 55 | 0.1 | 1 | C | 0.05M | 4.1 | 88 |
| Ex. 35 | Td. r. | 0.05 | 35 | 55 | 0.05 | 1 | C | 0.05M | 4.1 | 91 |
| Ex. 36 | Td. r. | 0.02 | 35 | 55 | 0.02 | 1 | C | 0.05M | 4.1 | 77 |
| Ex. 37 | Td. r. | 0.01 | 35 | 55 | 0.01 | 1 | C | 0.05M | 4.1 | 100 |
| Comp. 15 | Td. r. | 1 | — | — | — | — | C | 0.05M | 4.2 | 100 |
| Comp. 16 | Td. r | 0.5 | — | — | — | — | C | 0.05M | 4.1 | 100 |
| Comp. 17 | Td. r. | 0.1 | — | — | — | — | C | 0.05M | 4.1 | 100 |
| Comp. 18 | Td. r. | 0.05 | — | — | — | — | C | 0.05M | 4.1 | 100 |
| Comp. 19 | Td. r. | 0.02 | — | — | — | — | C | 0.05M | 4.1 | 100 |
| Comp. 20 | Td. r. | 0.01 | — | — | — | — | C | 0.05M | 4.1 | 100 |

SEn: Saccharification enzyme derived from
Td. r.: *Trichoderma reesei*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharification enzyme not immobilized on colloidal silica
pH-Adjuster
C: Na acetate buffer (pH = 4.0)

TABLE 8

| | Reaction temp. ° C. | Saccharification rate day 3 % | Saccharification rate day 14 % |
|---|---|---|---|
| Ex. 32 | 24 | 80 | 95 |
| Ex. 33 | 24 | 66 | 95 |
| Ex. 34 | 24 | 43 | 63 |
| Ex. 35 | 24 | 23 | 43 |
| Ex. 36 | 24 | 13 | 26 |
| Ex. 37 | 24 | 8 | 18 |
| Comp. Ex. 15 | 24 | 68 | 85 |
| Comp. Ex. 16 | 24 | 54 | 80 |
| Comp. Ex. 17 | 24 | 34 | 47 |
| Comp. Ex. 18 | 24 | 18 | 38 |
| Comp. Ex. 19 | 24 | 9 | 23 |
| Comp. Ex. 20 | 24 | 6 | 15 | adjusted by deionized water instead of addition of colloidal silica. Table 9 shows the saccharification enzyme compositions.

For producing corresponding saccharification reaction mixtures, the procedure of each of Examples 1 to 8 was repeated, except that the amount of microcrystalline cellulose powder was changed to 5.0 mass %. Regarding sugar production method, the procedure of each of Examples 1 to 8 was repeated, except that the enzymatic reaction period was changed to 7 days, and the reaction temperature was changed to 40° C. or 50° C. Determination of saccharification reaction efficiency was performed in the same manner as employed in Examples 1 to 8. Table 10 shows the results of saccharification rate measurement.

As is clear from FIG. 10, a high saccharification rate was attained when the saccharification enzyme to colloidal silica mass ratio (saccharification enzyme/colloidal silica) was 0.002 to 0.1, in the case of a saccharification reaction mixture having a ratio of the amount of the saccharification enzyme not immobilized on colloidal silica to the entire amount of the saccharification enzyme of 25% to 100%. Thus, a higher saccharification rate was attained, as compared with the case where the saccharification reaction mixture contained no colloidal silica.

Saccharification Enzyme Composition of Example 44

A cellulase aqueous solution (i.e., a saccharification enzyme aqueous solution) was prepared in the following manner. As a cellulase, a cellulase (product of MP biomedicals), having an optimum enzymatic activity at a pH of 3 to 6 and being derived from the *Aspergillus niger*) was used.

Firstly, cellulase powder (2.0 g) was added to deionized water (38 g), and the mixture was stirred at room temperature for 2 hours by means of a magnetic stirrer, to thereby prepare a 5 mass % cellulase aqueous solution. Subsequently, an acidic silica sol (pH: 2.9, silica concentration: 20 mass) (5.0 g), in which both solid and herical colloidal silica (mean primary particle size: 45 nm, and particle size measured through a dynamic light scattering method: 75 nm) prepared through the water glass method was dispersed in water, deionized water (12.0 g) and the aforementioned 5 mass % cellulase aqueous solution (2.0 g) were added under stirring. For the purpose adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %.

TABLE 9

| | SEn | SEn C. mass % | MPPS nm | PS nm | SC mass % | SE/CS by mass | pH-adjuster type | concn. | pH | Ratio % |
|---|---|---|---|---|---|---|---|---|---|---|
| Ex. 38 | Td. r. | 0.5 | 35 | 55 | 5 | 0.1 | C | 0.05M | 4.1 | 49 |
| Ex. 39 | Td. r. | 0.5 | 35 | 55 | 5 | 0.1 | C | 0.05M | 4.1 | 49 |
| Comp. 21 | Td. r. | 0.5 | — | — | — | — | C | 0.05M | 4.1 | 100 |
| Comp. 22 | Td. r. | 0.5 | — | — | — | — | C | 0.05M | 4.1 | 100 |
| Ex. 40 | Td. r. | 0.5 | 35 | 55 | 5 | 0.1 | I | 0.05M | 5.8 | 63 |
| Comp. 23 | Td. r. | 0.5 | — | — | — | — | I | 0.05M | 6.0 | 100 |
| Ex. 41 | Td. r. | 0.05 | 35 | 55 | 5 | 0.01 | E | 0.05M | 5.0 | 31 |
| Ex. 42 | Td. r. | 0.05 | 35 | 55 | 5 | 0.01 | E | 0.05M | 5.0 | 31 |
| Comp. 24 | Td. r. | 0.05 | — | — | — | — | E | 0.05M | 5.0 | 100 |
| Comp. 25 | Td. r. | 0.05 | — | — | — | — | E | 0.05M | 5.0 | 100 |
| Ex. 43 | Td. r. | 0.01 | 35 | 55 | 5 | 0.002 | E | 0.05M | 5.0 | 43 |
| Comp. 26 | Td. r. | 0.01 | — | — | — | — | E | 0.05M | 5.0 | 100 |

SEn: Saccharification enzyme derived from
Td. r.: *Trichoderma reesei*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharification enzyme not immobilized on colloidal silica
pH-Adjuster
C: Na acetate buffer (pH = 4.0)
E: Na acetate buffer (pH = 5.0)
I: Na acetate buffer (pH = 6.0)

TABLE 10

| | Reaction temp. °C. | Saccharification rate day 3 % | Saccharification rate day 7 % |
|---|---|---|---|
| Ex. 38 | 40 | 72 | 85 |
| Ex. 39 | 50 | 69 | 84 |
| Comp. Ex. 21 | 40 | 61 | 73 |
| Comp. Ex. 22 | 50 | 64 | 75 |
| Ex. 40 | 50 | 59 | 78 |
| Comp. Ex. 23 | 50 | 51 | 70 |
| Ex. 41 | 40 | 25 | 37 |
| Ex. 42 | 50 | 34 | 47 |
| Comp. Ex. 24 | 40 | 22 | 33 |
| Comp. Ex. 25 | 50 | 28 | 39 |
| Ex. 43 | 50 | 11 | 16 |
| Comp. Ex. 26 | 50 | 5 | 9 |

Saccharification Enzyme Composition of Example 45

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyalumium chloride, product of Taimei Chemicals Co., Ltd.) (7 ppm), and the aforementioned 5 mass % cellulase aqueous solution (2.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %.

Saccharification Enzyme Composition of Example 46

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (10 ppm), and the aforementioned 5 mass % cellulase aqueous solution (2.0 g) were added under stirring. For the purpose of pH adjustment 1M acetic acid-Na acetate buffer (pH: 4. (1.0 g) was added to the silica sol mixture, thereby yield a saccharification enzyme composition having a silica concentration of 5 mass % and a cellulase concentration of 0.5 mass %.

Saccharification Enzyme Composition of Example 47

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (14 ppm), and the aforementioned 5 mass % cellulase aqueous solution (2.0 g) were added under stirring. For the purpose of pH adjustment, 1M acetic acid-Na acetate buffer (ph: 4.0) (1.0 g) was added to the silica sol mixture, to thereby yield a saccharification enzyme composition having a silica concentration of 5 mass % and a cellulase concentration of 0.5 mass %.

Saccharification Enzyme Composition of Example 48

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (15 ppm), and the aforementioned 5 mass % cellulase aqueous solution (2.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %.

Saccharification Enzyme Composition of Example 49

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (16 ppm), and the aforementioned 5 mass % cellulase aqueous solution (2.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %.

Saccharification Enzyme Composition of Comparative Example 27

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (20 ppm), and the aforementioned 5 mass cellulase aqueous solution (2.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of 0.5 mass %.

Saccharification Enzyme Composition of Comparative Example 28

To an acidic silica sol (pH: 2.9, silica concentration: 20 mass %) (5.0 g), in which both solid and spherical colloidal silica (mean primary particle size: 45 nm, and particle size measured through a dynamic light scattering method: 75 nm) prepared through the water glass method was dispersed in water, deionized water (12.0 g), Alfine 83 (polyaluminum chloride, product of Taimei Chemicals Co., Ltd.) (27 ppm), and the aforementioned. 5 mass % cellulase aqueous solution (2.0 g) were added under stirring. For the purpose of pH adjustment, 1M acetic acid-Na acetate buffer (pH: 4.0) (1.0 g) was added to the silica sol mixture, to thereby yield a saccharification enzyme composition having a silica concentration of 5 mass % and a cellulase concentration of mass %.

Saccharification Enzyme Compositions of Comparative Example 29

The procedure of any of Examples 44 to 49 was repeated, except that the saccharification enzyme concentration was adjusted by deionized water instead addition of colloidal silica, to thereby prepare a saccharification enzyme composition containing no colloidal silica. Table 11 shows the saccharification enzyme composition.

Table 11 shows the saccharification enzyme compositions of Examples 44 to 49.

Production of each saccharification reaction mixture, and determination of saccharification reaction efficiency were performed in the same manner as employed in Examples 1 to 8. In the sugar production method, the procedure of each of Examples 1 to 8 was repeated, except that the enzymatic reaction period was changed to 7 days. Table 12 shows the results of saccharification rate measurement. FIG. 3 is a graph showing the dependency of the saccharification rate of the saccharification reaction mixture (each of Examples 44 to 49) on day 7 after enzymatic reaction, on the ratio of the amount of the saccharification enzyme not immobilized on colloidal silica contained in the saccharification reaction mixture to the entire amount of the saccharification enzyme contained therein. When the saccharification enzyme to colloidal silica mass ratio (saccharification enzyme/colloidal silica) and the pH were constant, the saccharification rate was found to be in response to the ratio of the amount of the saccharification enzyme not immobilized on colloidal silica to the entire amount of the saccharification enzyme. Specifically, a high saccharification rate was attained, in the case of a saccharification reaction mixture having a ratio of the amount of the saccharification enzyme not immobilized on colloidal silica to the entire amount of the saccharification enzyme of 27% to 77%.

TABLE 11

|  | SEn | SEn C. mass % | MPPS nm | PS nm | SC mass % | SE/CS by mass | pH-adjuster type | | pH | Ratio % |
|---|---|---|---|---|---|---|---|---|---|---|
| Ex. 44 | As. n. | 0.5 | 45 | 75 | 5 | 0.1 | C | 0.05M | 4.1 | 77 |
| Ex. 45 | As. n. | 0.5 | 45 | 75 | 5 | 0.1 | C | 0.05M | 4.1 | 66 |
| Ex. 46 | As. n. | 0.5 | 45 | 75 | 5 | 0.1 | C | 0.05M | 4.1 | 56 |
| Ex. 47 | As. n. | 0.5 | 45 | 75 | 5 | 0.1 | C | 0.05M | 4.1 | 41 |
| Ex. 48 | As. n. | 0.5 | 45 | 75 | 5 | 0.1 | C | 0.05M | 4.1 | 34 |
| Ex. 49 | As. n. | 0.5 | 45 | 75 | 5 | 0.1 | C | 0.05M | 4.1 | 27 |
| Comp. 27 | As. n. | 0.5 | 45 | 75 | 5 | 0.1 | C | 0.05M | 4.1 | 18 |
| Comp. 28 | As. n. | 0.5 | 45 | 75 | 5 | 0.1 | C | 0.05M | 4.1 | 11 |
| Comp. 29 | As. n. | 0.5 | — | — | — | — | C | 0.05M | 4.1 | 100 |

SEn: Saccharification enzyme derived from
As. n.: *Aspergillus niger*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharification enzyme not immobilized on colloidal silica
pH-Adjuster
C: Na acetate buffer (pH = 4.0)

TABLE 12

|  | Reaction temp. ° C. | Saccharification rate day 3 % | Ssaccharification rate day 7 % |
|---|---|---|---|
| Ex. 44 | 24 | 33 | 53 |
| Ex. 45 | 24 | 26 | 45 |
| Ex. 46 | 24 | 33 | 49 |
| Ex. 47 | 24 | 27 | 43 |
| Ex. 48 | 24 | 25 | 41 |
| Ex. 49 | 24 | 26 | 40 |
| Comp. Ex. 27 | 24 | 15. | 26 |
| Comp. Ex. 28 | 24 | 5 | 12 |
| Comp. Ex. 29 | 24 | 19 | 36 |

Saccharification Enzyme Composition of Comparative Example 30

Cellulase powder (1 g) was added to deionized water (9 g), and the mixture was stirred at room temperature for 2 hours by means of a magnetic stirrer, to thereby prepare a 10 mass % cellulase aqueous solution. Subsequently, deionized water (17.9 g) and the aforementioned 10 mass % cellulase aqueous solution (1.0 g) were added to precipitated silica powder (Carplex #80, product of DSL Japan) (mean primary particle size: 7 nm, and particle size measured through a dynamic light scattering method: 1,750 nm) (0.1 g), under stirring. For the purpose of pH adjustment, 1M acetic acid-Na acetate buffer (pH: 4.0) (1.0 g) was added to the silica mixture, to thereby yield a saccharification enzyme composition having a silica concentration of 5 mass % and a cellulase concentration of 0.5 mass %.

Saccharification Enzyme Composition of Comparative Example 31

Under stirring, deionized water (17.9 and the aforementioned 10 mass cellulase aqueous solution (1.0 g) were added to precipitated silica powder (Tokusil GU-N, product of Tokuyama) (mean primary particle size: 11 nm, and particle size measured through a dynamic light scattering method: 4,740 nm) (0.1 g). For the purpose of pH adjustment, 1M acetic acid-Na acetate buffer (pH: 4.0) (1.0 g) was added to the silica mixture, to thereby yield a saccharification enzyme composition having a silica concentration of 5 mass % and a cellulase concentration of 0.5 mass %.

Table 13 shows the saccharification enzyme compositions of Comparative Examples 30 and 31.

Production of each saccharification reaction mixture, sugar production method, and determination of saccharification reaction efficiency were performed in the same manner as employed in Examples 1 to 8. Table 14 shows the results of saccharification rate measurement. Differing from colloidal silica, precipitated silica powder was found to fail to enhance saccharification rate.

TABLE 13

|  | SEn | SEn C. mass % | MPPS nm | PS nm | SC mass % | SE/CS by mass | pH-adjuster type | | pH | Ratio % |
|---|---|---|---|---|---|---|---|---|---|---|
| Ex. 28 | As. n. | 0.5 | 12 | 20 | 5 | 0.1 | C | 0.05M | 4.1 | 91 |
| Comp. 30 | As. n. | 0.5 | 7 | 1,750 | 5 | 0.1 | C | 0.05M | 4.2 | 68 |
| Comp. 31 | As. n. | 0.5 | 11 | 4,740 | 5 | 0.1 | C | 0.05M | 4.2 | 64 |
| Comp. 33 | As. n. | 0.5 | — | — | — | — | C | 0.05M | 4.1 | 100 |

SEn: Saccharification enzyme derived from
As. n.: *Aspergillus niger*
SEn C.: Saccharification enzyme concentration
MPPS: Mean primary particle size
PS: Particle size measured through dynamic light scattering method
SC: Silica concentration
SE/CS: Saccharification enzyme/colloidal silica
Ratio: the ratio of the amount of the saccharification enzyme not immobilized on colloidal silica
pH-Adjuster
C: Na acetate buffer (pH = 4.0)

TABLE 14

|  | Reaction temp. °C. | Saccharification rate day 3 % | Saccharification rate day 14 % |
|---|---|---|---|
| Ex. 28 | 24 | 34 | 67 |
| Comp. Ex. 30 | 24 | 26 | 57 |
| Comp. Ex. 31 | 24 | 25 | 57 |
| Comp. Ex. 13 | 24 | 19 | 57 |

The invention claimed is:

1. A saccharification reaction mixture for saccharifying at least one of cellulose and hemicellulose via an enzymatic reaction, the reaction mixture comprising, in a dispersion state:
    at least one of cellulose and hemicellulose,
    a saccharification enzyme including an enzyme derived from the genus *Aspergillus* or the genus *Trichoderma*, and
    colloidal silica having a mean primary particle size of 1 nm to 400 nm, and a particle size, as measured through a dynamic light scattering method, of 5 nm or greater and less than 500 nm,
    wherein:
        a saccharification enzyme concentration is 0.005 mass % to 3.0 mass %,
        a colloidal silica concentration is 0.005 mass % to 40 mass %,
        the ratio by mass of the saccharification enzyme to the colloidal silica (saccharification enzyme/colloidal silica) is 0.002 to 300,
        a pH is 3 to 11, and
        the ratio of the amount of the saccharification enzyme not immobilized on colloidal silica to the entire amount of the saccharification enzyme is 50% to 100% at a start of the enzymatic reaction.

2. A saccharification enzyme composition for saccharifying at least one of cellulose and hemicellulose via an enzymatic reaction, the enzyme composition comprising, in a dispersion state:
    a saccharification enzyme including an enzyme derived from the genus *Aspergillus* or the genus *Trichoderma*, and
    colloidal silica having a mean primary particle size of 1 nm to 400 nm, and a particle size, as measured through a dynamic light scattering method, of 20 nm or more and less than 500 nm,
    wherein the ratio of the amount of the saccharification enzyme not immobilized on colloidal silica to the entire amount of the saccharification enzyme is 50% to 100% at a start of the enzymatic reaction.

3. A saccharide production method comprising employing the saccharification reaction mixture recited in claim 1 to thereby form a saccharide.

* * * * *